(12) United States Patent
Yamaya (10) Patent No.: US 10,820,785 B2
(45) Date of Patent: Nov. 3, 2020

(54) COVER REMOVAL TOOL FOR ENDOSCOPE

(71) Applicant: OLYMPUS CORPORATION, Tokyo (JP)

(72) Inventor: Koji Yamaya, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 187 days.

(21) Appl. No.: 15/860,023

(22) Filed: Jan. 2, 2018

(65) Prior Publication Data

US 2018/0140171 A1    May 24, 2018

Related U.S. Application Data (63) Continuation of application No. PCT/JP2016/067414, filed on Jun. 10, 2016.

(30) Foreign Application Priority Data

Jul. 6, 2015    (JP) .................. 2015-135339

(51) Int. Cl.
*A61B 1/00* (2006.01)
*G02B 23/24* (2006.01)

(52) U.S. Cl.
CPC ...... *A61B 1/00137* (2013.01); *A61B 1/00062* (2013.01); *A61B 1/00098* (2013.01);
(Continued)

(58) Field of Classification Search
CPC .............. A61B 1/00137; A61B 1/0089; A61B 1/00096; A61B 1/00101
See application file for complete search history.

(56) References Cited

U.S. PATENT DOCUMENTS 4,881,810 A * 11/1989 Hasegawa .......... A61B 1/00101
356/241.5
5,569,157 A    10/1996 Nakazawa et al.
(Continued)

FOREIGN PATENT DOCUMENTS

| JP | H07-184838 A | 7/1995 |
| JP | H07-313439 A | 12/1995 |
| JP | 4855824 B2 | 1/2012 |

OTHER PUBLICATIONS

English translation of International Preliminary Report on Patentability dated Jan. 18, 2018 together with the Written Opinion received in related International Application No. PCT/JP2016/067414.
(Continued)

*Primary Examiner* — Matthew J Kasztejna
(74) *Attorney, Agent, or Firm* — Scully, Scott, Murphy & Presser, P.C.

(57) ABSTRACT

The cover removal tool of the endoscope includes an enclosure, which is a fit hole that is fitted to cover the distal end cover having a locking portion and mounted on the distal end assembly, which is provided at the tip of the insertion section. The cover removal tool is provided with a protrusion that protrudes inside the enclosure. When the cover removal tool is fitted with the distal end cover being into contact with its interior, the protrusion comes into contact with part of the edge of the opening of the distal end cover and pushes in the peripheral direction. As the edge of the opening is pressed while being twisted, the distal end cover is broken by plastic deformation, and the lock with the locking portion is thereby released.

10 Claims, 11 Drawing Sheets

(52) U.S. Cl.
CPC ...... *A61B 1/00101* (2013.01); *A61B 1/00091* (2013.01); *G02B 23/2476* (2013.01)

(56) References Cited

U.S. PATENT DOCUMENTS

| | | | | |
|---|---|---|---|---|
| 5,662,588 | A | * | 9/1997 | Iida .................... A61B 1/00091 600/121 |
| 5,685,823 | A | | 11/1997 | Ito et al. |
| 5,707,344 | A | * | 1/1998 | Nakazawa ........... A61B 1/0008 600/107 |
| 5,730,701 | A | * | 3/1998 | Furukawa ............ A61B 1/0008 600/121 |
| 5,860,913 | A | * | 1/1999 | Yamaya ............. A61B 1/00091 600/121 |
| 6,878,107 | B2 | * | 4/2005 | Hino .................... A61B 1/0008 600/121 |
| 8,038,604 | B2 | | 10/2011 | Hamazaki et al. |
| 9,949,619 | B2 | * | 4/2018 | Iizuka ...................... A61B 1/00 |

OTHER PUBLICATIONS

International Search Report dated Sep. 6, 2016 issued in PCT/JP2016/067414.
Japanese Office Action dated Apr. 11, 2017 in Japanese Patent Application No. 2017-512069.

\* cited by examiner

COVER REMOVAL TOOL FOR ENDOSCOPE

CROSS-REFERENCE TO RELATED APPLICATIONS

This is a Continuation Application of PCT Application No. PCT/JP2016/067414, filed Jun. 10, 2016, which was published under PCT Article 21(2) in Japanese.

This application is based upon, and claims the benefit of priority from, the Japanese Patent Application No. 2015-135339, filed Jul. 6, 2015, the entire contents of which are incorporated herein by reference.

BACKGROUND OF THE INVENTION

1. Field of the Invention

The present invention relates to a cover removal tool for removing a distal end cover attached to a distal end assembly of a flexible tube of an endoscope, and to an endoscopic system.

2. Description of the Related Art

Insertion devices of endoscopes in general, such as flexible tubes, have a distal end assembly with an opening therein. Treatment tools having various functions are inserted through the channel and extend out of this opening. Examples of such treatment tools include a high-frequency treatment tool with which a resection treatment may be conducted onto living tissue using a high-frequency current.

Normally, a distal end assembly is configured by combining multiple metallic members. For this reason, when the inserted high-frequency treatment tool is in contact with or in the vicinity of the metallic members, a high-frequency current may flow through these metallic members, or the members may be used as part of the current feedback path. Thus, when introducing the high-frequency treatment tool into a lumen of a living body, shielding measures need to be provided so that the high-frequency current will not flow into the living tissue other than the treatment targeted area. For such measures, a distal end cover is attached to the distal end assembly of the insertion section to cover the exposed metallic members.

For instance, Patent Document 1: Japanese Patent No. 4855824 suggests a cap-shaped distal end cover formed of a resin material. This distal end cover includes a locking portion having a plastic deformation portion. When removing the cover, the finger hooking portion of the engaging portion is pushed open with the fingers. This deforms the distal end cover so that the reuse of the cover can be prevented.

The present invention offers a distal end cover for an endoscope, which facilitates the attachment to the distal end assembly of the insertion section of the endoscope, exhibits the function of preventing the leakage of the high-frequency current, and facilitates the detachment with a simple operation.

BRIEF SUMMARY OF THE INVENTION

According to an embodiment of the present invention, there is provided an endoscopic cover removal tool configured to remove a distal end cover, the distal end cover being attached to a distal end assembly arranged at a distal end of an insertion section of an endoscope that is to be inserted into a lumen, the cover removal tool comprising: an enclosure configured to cover a periphery of the distal end cover; and a protrusion configured to enter an opening of the distal end cover when the distal end cover is in contact with an interior of the enclosure, being able to press the distal end cover in contact with the distal end cover, and extending from an inner surface of the enclosure.

In addition, an endoscopic system according to an endoscopic system comprising: an endoscope including an insertion section that is to be inserted into a lumen, and a distal end cover attached to a distal end assembly arranged at a distal end of the insertion section; and a distal cover removal tool, comprising: an enclosure configured to cover a periphery of the distal end cover; and a protrusion configured to enter an opening of the distal end cover, being able to press the distal end cover in contact with the distal end cover, and extending from an inner surface of the enclosure.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

One embodiment of the present invention will be described with reference to the accompanying drawings.

First Embodiment

Figure 1:
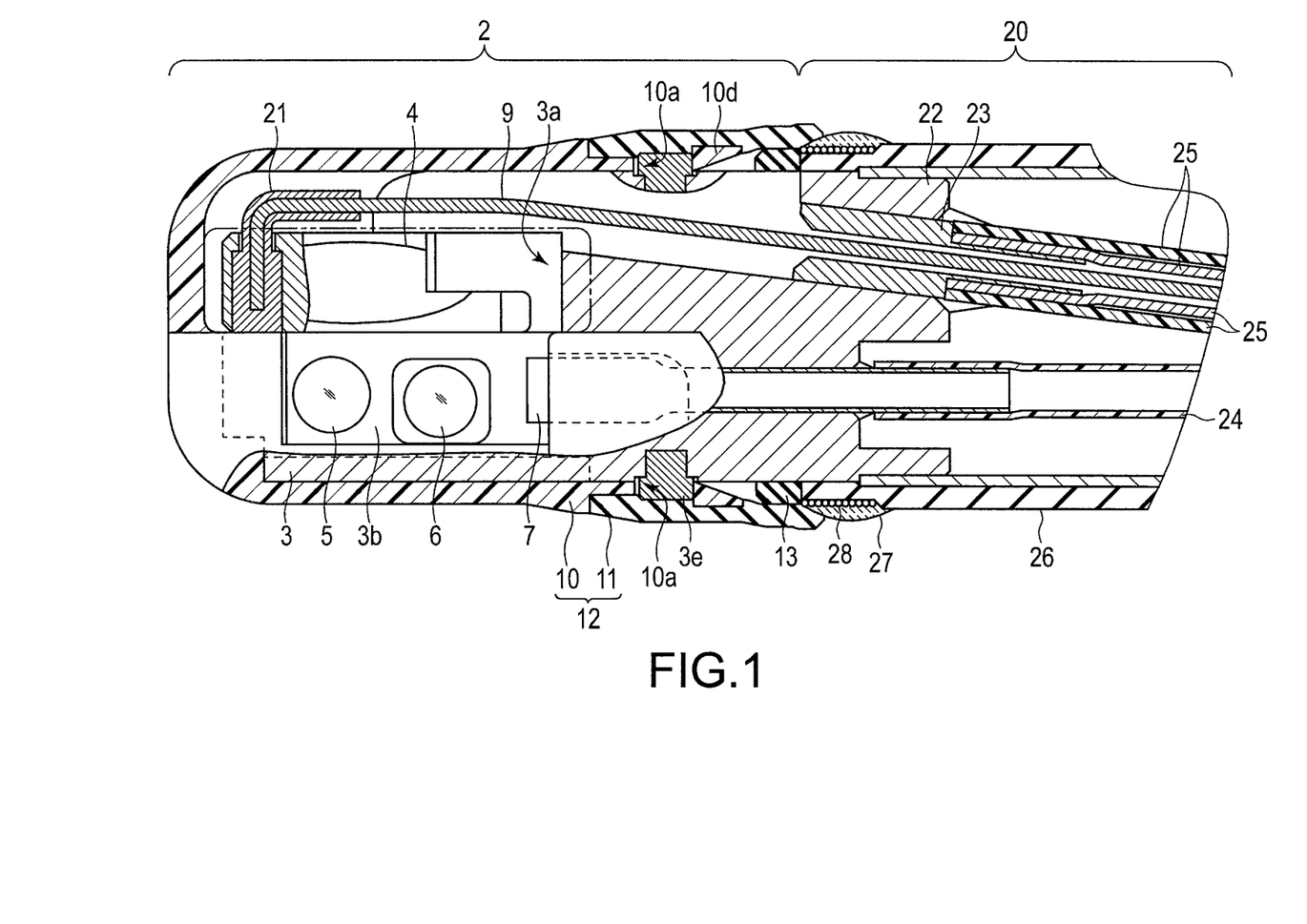
FIG. 1 is a cross section of the structure of a distal end assembly of an endoscope according to the first embodiment with a distal end cover attached, when viewed from above.
Figure 2:
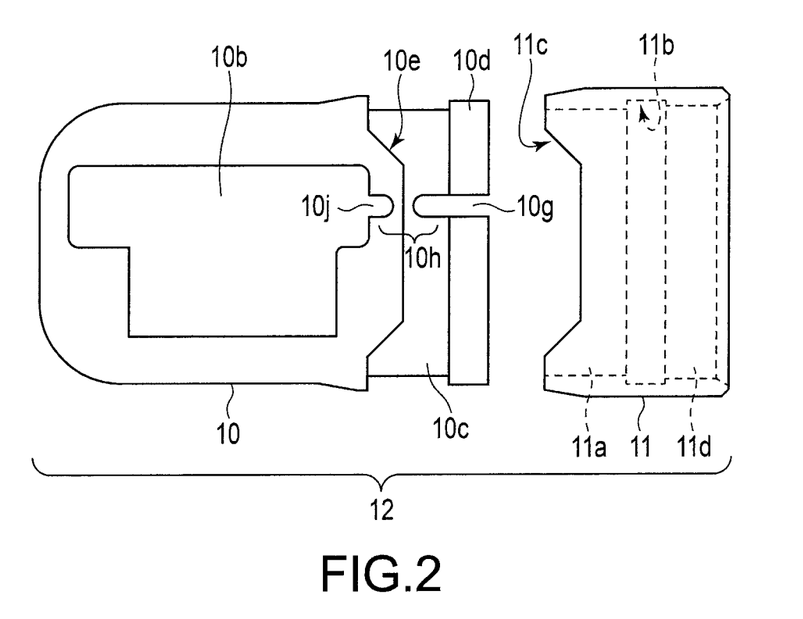
FIG. 2 is a diagram showing the outer appearance of the distal end cover that is separated, when viewed from above.
Figure 3:
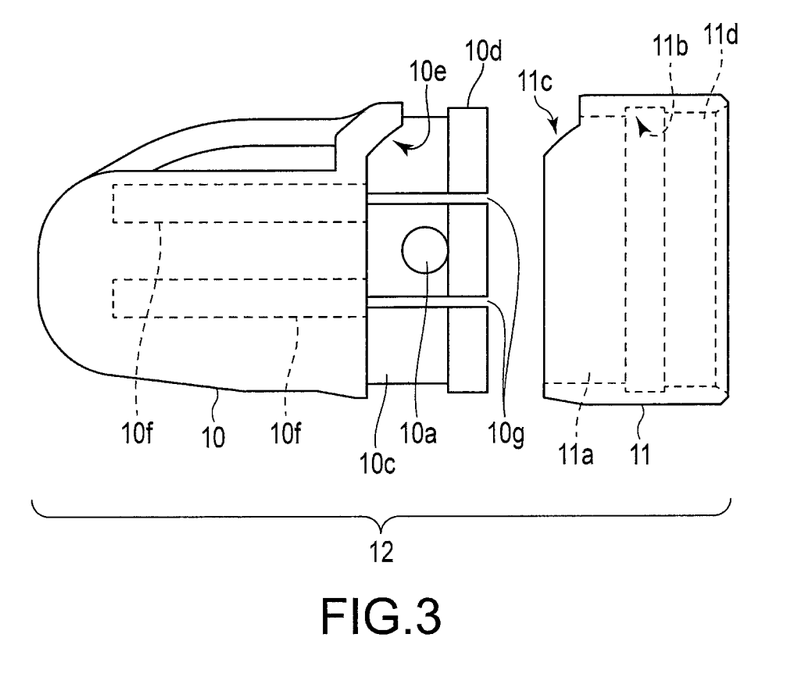
FIG. 3 is a diagram showing the outer appearance of the distal end cover that is separated, when viewed from its side.
Figure 4:
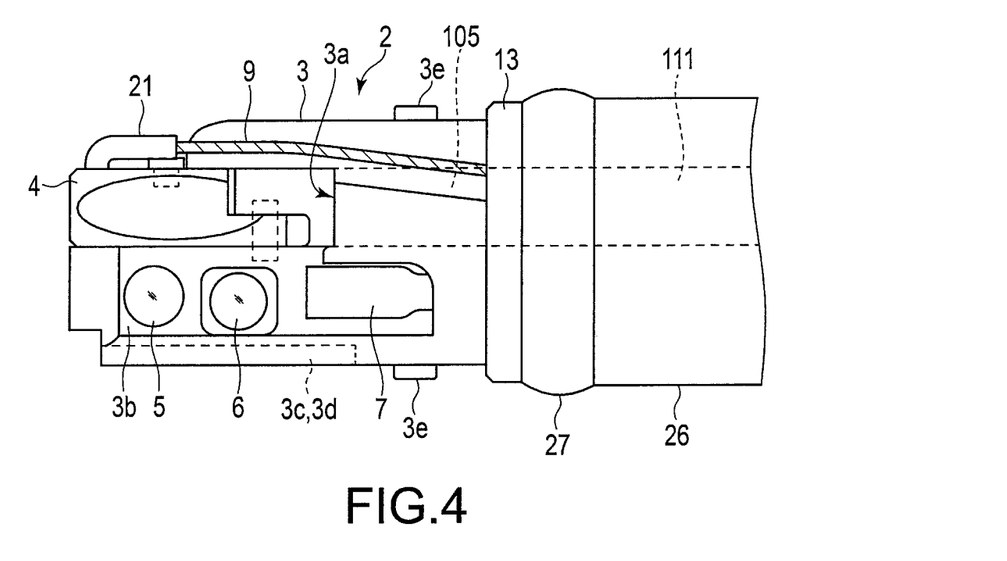
FIG. 4 is a diagram showing the outer appearance of the distal end assembly without a distal end cover attached, when viewed from above.
Figure 5:
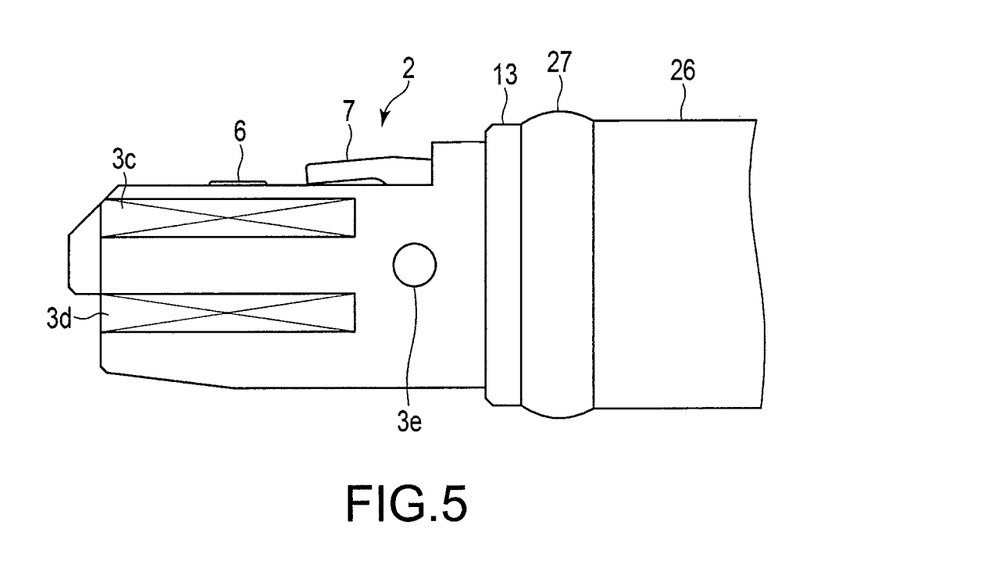
FIG. 5 is a diagram showing the outer appearance of the distal end assembly without a distal end cover attached, when viewed from its side.
Figure 17:
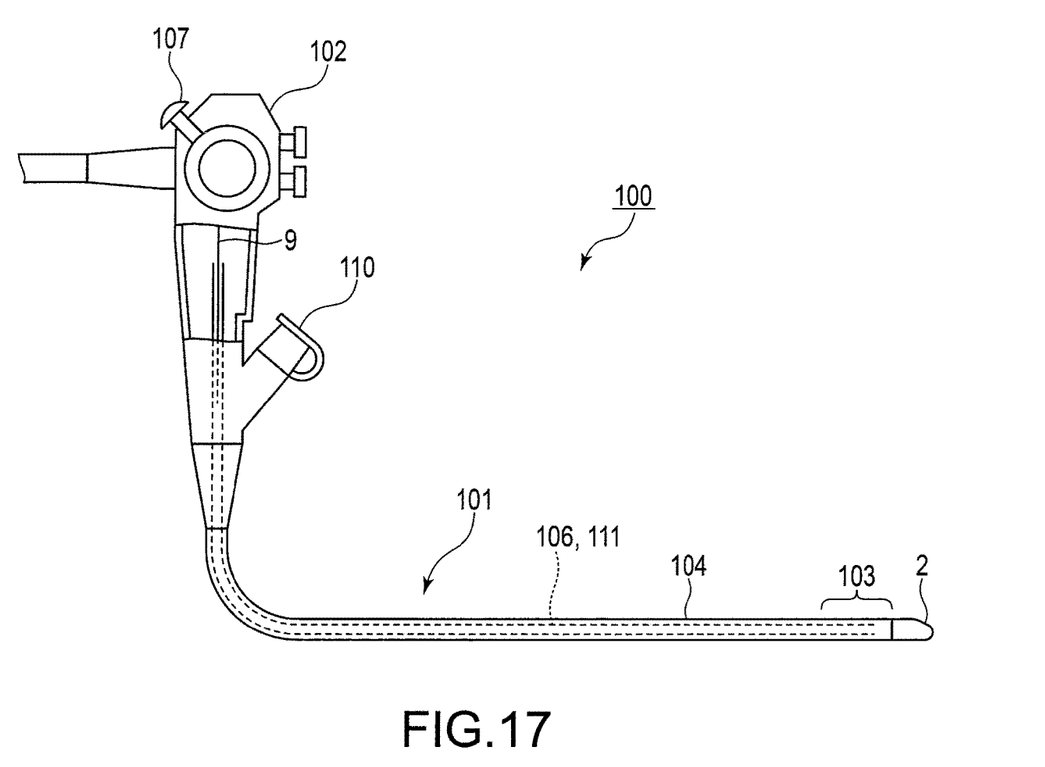
FIG. 17 is a diagram showing an example structure of the distal end assembly of the insertion device applied to the distal end assembly of an insertion section of an endoscope.

FIG. 1 is a cross section of the structure of a distal end assembly of an endoscope according to the first embodiment with a distal end cover attached, when viewed from above. FIG. 2 is a diagram showing the outer appearance of the distal end cover that is separated, when viewed from above. FIG. 3 is a diagram showing the outer appearance of the distal end cover that is separated, when viewed from its side. FIG. 4 is a diagram showing the outer appearance of the distal end assembly without the distal end cover, when viewed from above. FIG. 5 is a diagram showing the outer appearance of the distal end assembly without the distal end cover, when viewed from its side. FIG. 17 is a diagram showing the structure of the distal end assembly of the insertion device according to the present embodiment applied to the distal end assembly of an insertion section of an endoscope.

An example structure of a distal end assembly of an insertion section of an endoscope in which a swing base (or riser) configured to change the moving direction of an inserted high-frequency treatment tool is arranged will be explained. This swing base may be a swing mechanism for vertically changing the moving direction, or for vertically and horizontally changing the direction. In the following embodiment, the structure of the treatment tool being a high-frequency treatment tool is discussed, but the structure is not limited thereto.

An endoscope 100 includes an insertion section 101 that is to be inserted to a pipe or lumen, and an operation section 102. On the proximal side of the insertion section 101, an insertion port (forceps port) 110 is provided for a treatment tool that performs an electrical treatment such as a treatment using a high-frequency current onto a treatment targeted area. A cylindrical distal end assembly 2 is provided on the distal side of the insertion section 101. The operation section 102 is provided with a swing base operation section 107. This endoscope is provided with components common in any endoscopic system, although they are not shown, including a light source device for supplying illumination light, a controller that includes a video processor for performing image processing onto the captured video signals, a display unit for displaying observation images, and a storage unit for storing the video signals.

The insertion section 101 includes a bending portion 103 and a flexible tube 104 arranged continuously from the distal end assembly 2 on the proximal side thereof. A channel conduit 111 through which treatment tools are inserted, an air/water supply tube 106 for supplying a cleaning liquid and air, and a long traction wire (traction member) 9 for causing a swing movement (raising movement) on a swing base are included in the insertion section 101.

With this traction wire 9, the swing base is coupled to the swing base operation section 107. When the lever of the swing base operation section 107 is operated, the swing base 4 swings up (rotates) to rise or swings down to be laid.

The channel conduit 111 runs from an insertion port 110 provided on the proximal side through the flexible tube 104, is communicated with a treatment tool channel hole 105, and has a channel opening 3a at its tip (see FIG. 4). The high-frequency treatment tool is inserted through the insertion port 110, runs through the channel conduit 111, and extends out of the channel opening 3a of the treatment tool channel hole 105.

Next, the distal end assembly 2 will be explained by referring to FIGS. 1, 4, and 5.

The distal end assembly 2 mainly includes a base member 3 formed of a metallic material such as stainless steel, a swing base 4 rotatably provided on the base member 3, and an endoscopic cylindrical distal end cover 12 (hereinafter referred to as a distal end cover). The base member 3 and the outer member 26 of the distal portion side 20 of the bending portion 103 are secured by binding a thin fixation string 28. The outer member 26 is a watertight and insulating tube formed of resin or rubber. To cover the surface of the thin fixation string 28, a fixation ring 27 is formed by coating the thin fixation string 28 with an insulating resin material.

The base member 3 includes two parts along the longitudinal direction; one part includes the channel opening 3a and the swing base 4 arranged in front of the channel opening 3a, and the other part includes a flat observation surface 3b with respect to the outer peripheral surface. The channel opening 3a communicates with the insertion port 110 of the insertion section 101 by way of the treatment tool channel conduit 111. A lighting window 5 is arranged in the observation surface 3b, through which illumination light guided by an optical fiber that is not shown is incident. An observation window 6 is arranged adjacent to the lighting window 5. An imaging section is provided, although it is not shown, in which an optical system continuously coupled to the observation window 6 to form an optical image on an optical path, and an image pickup device that generates video signals from the optical image by photoelectric conversion, and an electric circuit that implements various processes on the video signals, are arranged.

A nozzle 7 is provided in the vicinity of the observation window 6 on the proximal side in the longitudinal axis direction so that air or a cleaning liquid, such as normal saline, supplied through an air/water supply tube 24 (106), is spurted to suitably clean the lighting window 5 and the observation window 6.

As illustrated in FIGS. 4 and 5, groove-shaped rotation regulation sections 3c and 3d are formed at least on the side surfaces of the base member 3 that are continuous from the observation surface 3b in such a manner as to extend in parallel in the longitudinal direction. The rotation regulation sections 3c and 3d are configured to regulate the rotation of the distal end cover 12 attached to the distal end assembly 2 in the peripheral direction. In addition, cylindrical locking pins 3e (first locking portions) are provided on the two side surfaces on the proximal side with respect to the rotation regulation sections 3c and 3d to be fitted into locking holes 10a of a first cover 10 provided in the distal end cover 12, which will be described later. The shape of the locking pins 3e is not limited to a cylinder, and may take any shape as long as it protrudes and establishes an engagement.

Figure 7:
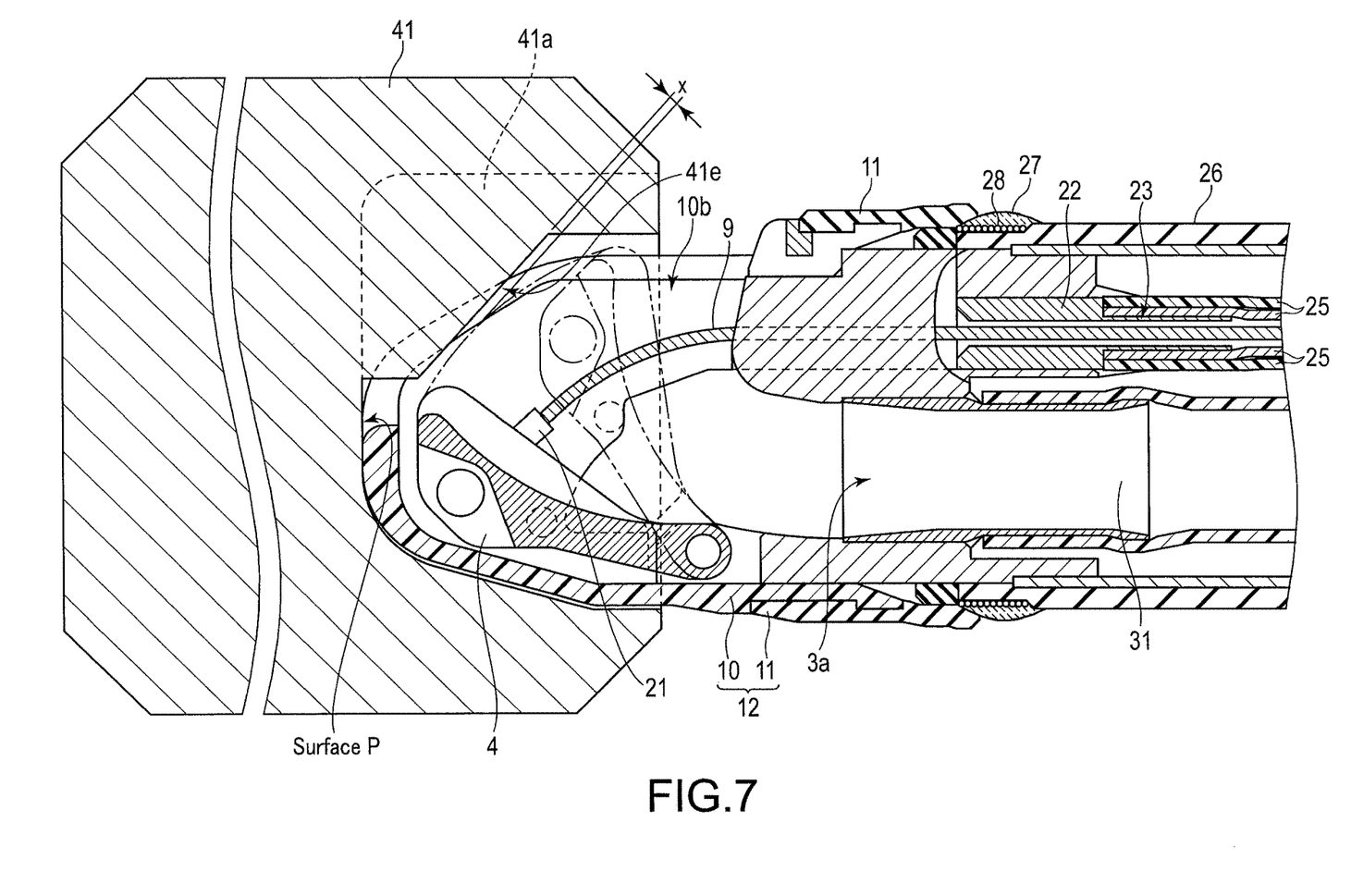
FIG. 7 is a cross section of the distal end cover attached to the distal end assembly, with the cover removal tool fitted thereon.

As illustrated in FIG. 7, which will be described later, the swing base 4 has a concaved contact surface with which the treatment tool (not shown) extending out of the channel opening 3a comes into contact and which changes the moving direction of the treatment tool. A connector 21 is provided on the outer surface of the swing base 4, to which the traction wire 9 is connected. The traction wire 9 is coupled to the swing base operation section 107 via a wire guide 25, which is fitted onto a connector 23 secured by the guide 22. When the connector 21 is pushed or pulled by operating the lever of the swing base operation section 107, the swing base 4 rises or is laid in accordance with the connector 21. Furthermore, an insulation ring 13 having insulating properties is formed entirely around the periphery in such a manner as to be tightly attached to the end surfaces of the outer member 26 and thin fixation string 28. This insulation ring 13 is provided on the side of the operation section 102 with respect to the locking pins 3e and locking holes 10a that are locking portions. In other words, the insulation ring 13 is arranged on the outer periphery at the connecting portion between the distal end assembly 2 and the bending portion 103.

Next, the structure of the distal end cover 12 will be explained with reference to FIGS. 2 and 3.

The distal end cover 12 according to the present embodiment includes the first cover 10 and second cover 11, which have different effects and functions. Of these covers, the first cover 10 is formed of an insulating elastic-plastic resin material such as plastic and injection-molded into a cylindrical cup, with its distal side closed. The distal side is shaped into a curve, and its surface is smooth and demonstrates excellent sliding properties. The second cover 11 is formed of an insulating, elastic material, such as rubber, into a loop.

The first cover 10 is provided with an opening (window) 10b to expose the swing base 4, lighting window 5 and observation window 6 arranged in the distal end assembly 2 to which the first cover 10 is to be attached. In the following explanation, the surface in which the opening 10b is provided is defined as a top surface. The direction from the distal portion to the proximal portion (the opening side) is defined as the longitudinal direction, and the direction orthogonal to the longitudinal direction is the peripheral direction.

The first cover 10 includes on its proximal side a contact surface 10c, which is stepped lower than the outer peripheral surface around the entire periphery. At the edge of the opening side of the contact surface 10c, a fit portion 10d is formed, creating a step to have an increased thickness, and demonstrates a locking function. As shown in FIG. 1, the fit portion 10d is formed with its inside surface tapered toward the opening so as to facilitate the fitting onto the distal end assembly 2.

Circular locking holes (or circular grooves) 10a are provided in the two side surfaces of the contact surface 10c to engage with the locking pins 3e of the distal end assembly 2 so as to prevent the cover from coming off. Furthermore, on the two side surfaces of the contact surface 10c, multiple linear slits 10g are provided to extend in the longitudinal direction so as to elastically pull out the portion including the locking holes 10a when fitting onto the distal end assembly 2. On the inner surface of the first cover 10 extending from the distal side to the contact surface 10c, rotation preventing convex portions 10f are formed to be engaged with the rotation regulation sections 3c and 3d. The rotation preventing convex portions 10f are multiple (two in this example) bar-shaped convex portions extending in parallel in the longitudinal direction. A brittle portion 10h is defined by a notch 10j from the side of the opening 10b and the slit 10g from the edge of the fit portion 10d, where the notch j and the slit 10g are aligned in the longitudinal direction. This brittle portion 10h is where the first cover 10 breaks, for example, by twisting the first cover 10.

The second cover 11 is formed of an insulating, elastic material such as rubber, into a loop. A proximal-side contact surface 11c is formed so as to fit a distal-side contact surface 10e of the contact surface 10c of the first cover and thereby create a smooth connection between its outer peripheral surface and the outer peripheral surface of the first cover 10.

The inner peripheral surface of the second cover 11 is provided with a contact surface 11a on the distal side so as to be tightly fitted onto the contact surface 10c when the second cover 11 is engaged with the first cover 10. A fit groove 11b is provided to continue from the proximal side of the contact surface 11a and to be engaged with the fit portion 10d. The inner peripheral surface of the second cover 11 on the proximal side is formed into a contact surface 11d, which is to be tightly fitted onto the distal end assembly 2.

The second cover 11, when being fitted on the first cover 10 and the insulation ring 13 of the distal end assembly 2, produces elastic force on these components toward the center. This elastic force may be produced, for example, by reducing the inner diameter of the second cover 11 with respect to the outer diameters of the first cover 10 and the insulation ring 13 of the distal end assembly 2.

In such a structure, when the first cover 10 and the second cover 11 are fitted together, an adhesive may be used. However, the adhesion force of the adhesive should be suitably chosen so that the first cover 10 will be easily separated from the second cover 11 when the brittle portion 10h of the first cover 10 is broken.

Figure 12:
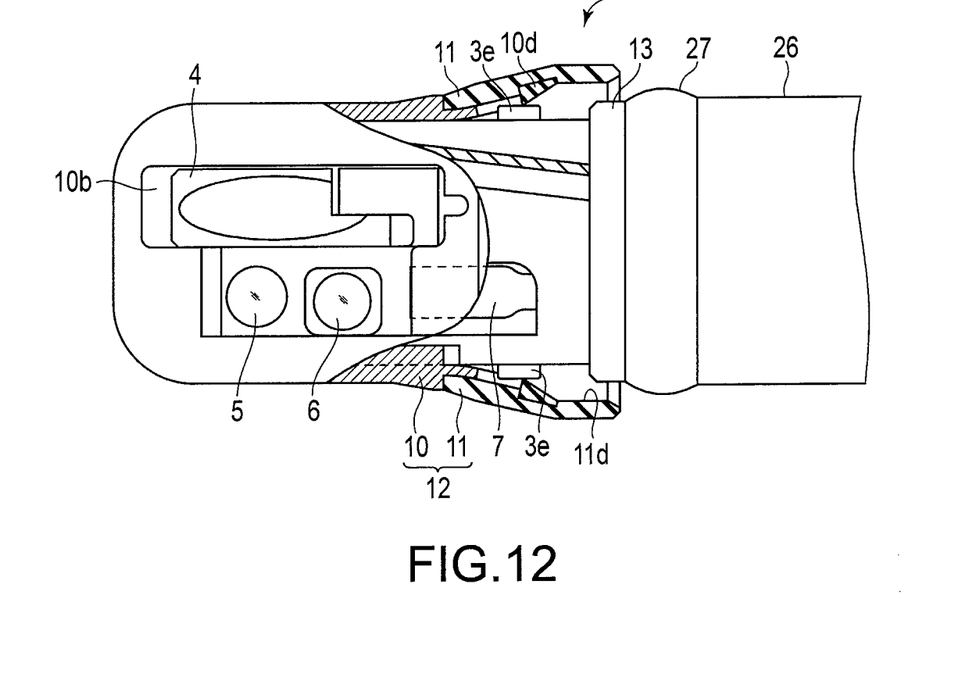
FIG. 12 is a partial cross section showing the state of the distal end cover attached to the distal end assembly.

The procedure and effects of the attachment of the first cover 10 and the second cover 11 to the distal end assembly 2 will be explained with reference to FIGS. 1-3 and 12. FIG. 12 is a partial cross section showing the state of the distal end cover attached to the distal end assembly.

First, the second cover 11 is fitted onto the first cover 10 from its proximal side so that the contact surface 10c and the contact surface 11a are brought into tight contact. Furthermore, the fit groove 11b is fitted onto the fit portion 10d. As a result, the structure becomes a unified body of the distal end cover 12 (or may be provided as a product in one unified body).

Next, the distal end cover 12 is slid onto the distal end assembly 2 to cover the distal end assembly 2. As illustrated in FIG. 12, the distal end cover 12 is inserted until the contact surface 11d of the second cover 11 covers further than the insulation ring 13 and comes into contact with the fixation ring 27. Here, the first cover 10 slides onto the distal end assembly 2 with the rotation preventing convex portions 10f engaged with the rotation regulation sections 3c and 3d so that the first cover 10 can be appropriately positioned when the locking pins 3e of the distal end assembly 2 are brought into lock with the locking holes 10a.

The distal end cover 12 according to the present embodiment prevents the high-frequency current of the distal end assembly 2 from leaking. The high-frequency treatment tool inserted through the insertion port 110 extends out of the channel opening 3a of the distal end assembly 2, and the direction of the travel of the tool is changed by the swing base 4. When a high-frequency current is used for the high-frequency treatment tool to execute a treatment, the high-frequency wave tends to propagate through the space, which causes the high-frequency current to flow into the distal end assembly 2. However, because of the second cover 11 and the insulation ring 13 tightly attached together, this high-frequency current will not leak from the attached portion to the outside of the distal end cover 12. Thus, the high-frequency current i will not leak from the back side of the distal end cover 12 that the operator is unable to see, and even if the distal end cover 12 happens to touch the living tissue in the lumen that is not the treatment targeted area, the possibility of inflicting a burn or other damage can be significantly reduced.

Figure 6A:
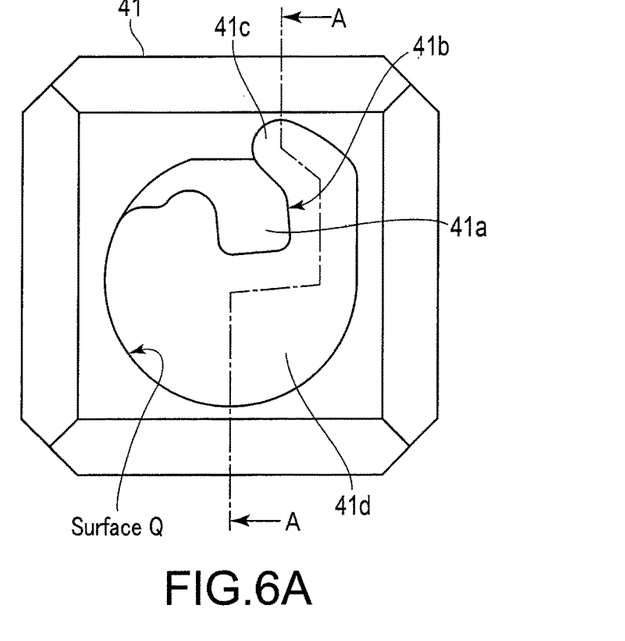
FIG. 6A is a diagram showing the structure of the cover removal tool when viewed from the front.
Figure 6B:
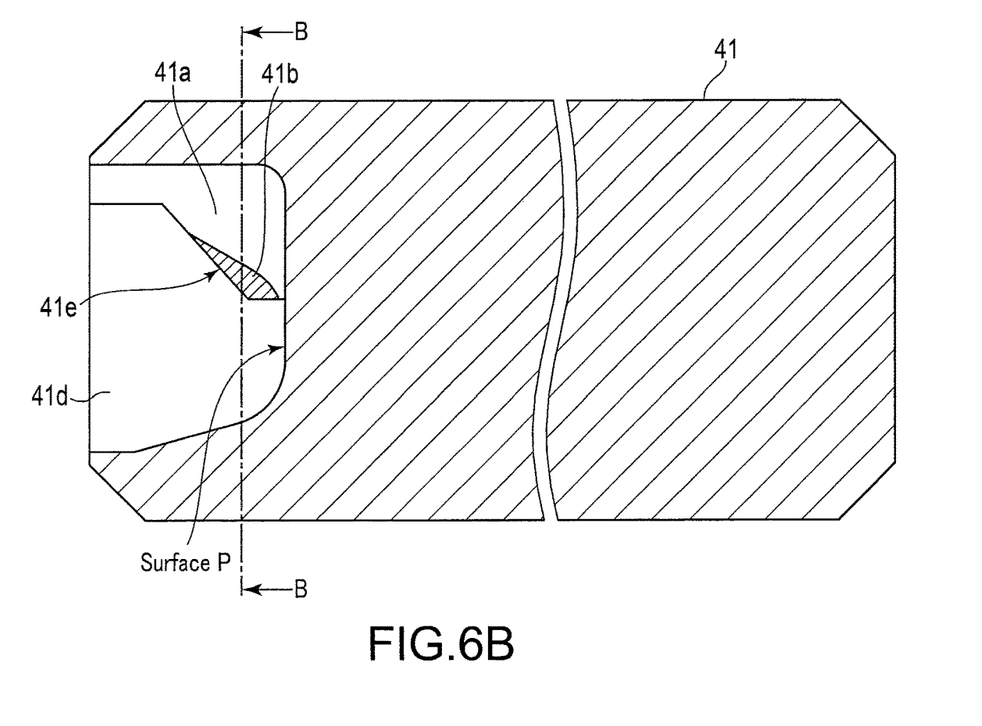
FIG. 6B is a cross section of the structure of the cover removal tool when viewed from its side.
Figure 8:
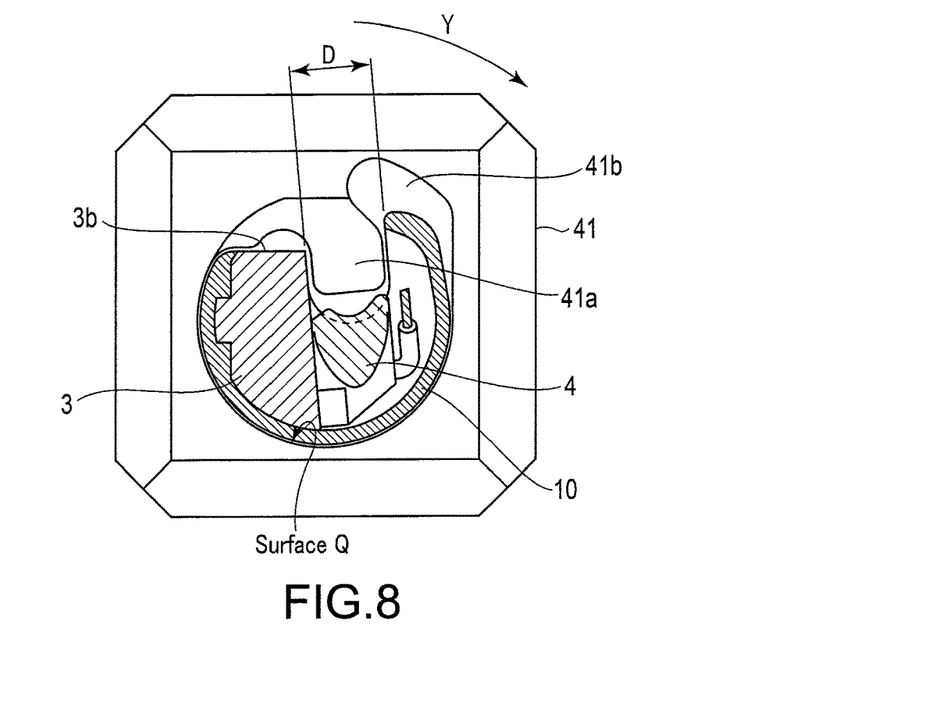
FIG. 8 is a cross section of the distal end cover with the cover removal tool fitted thereon, before the removal.
Figure 9:
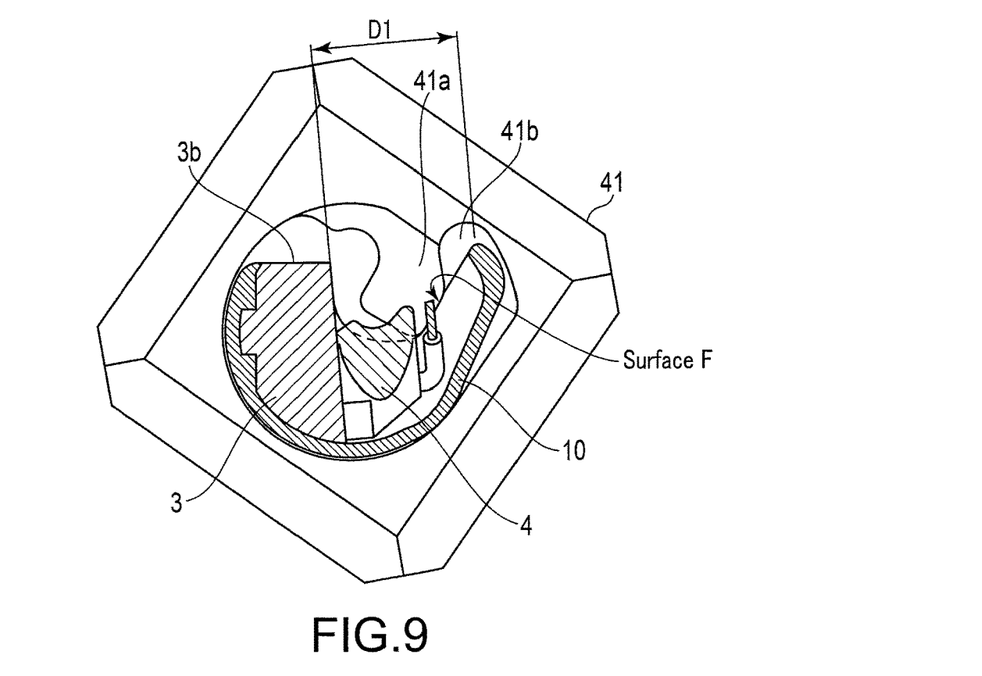
FIG. 9 is a cross section of the distal end cover with the cover removal tool fitted thereon, when being removed.
Figure 10:
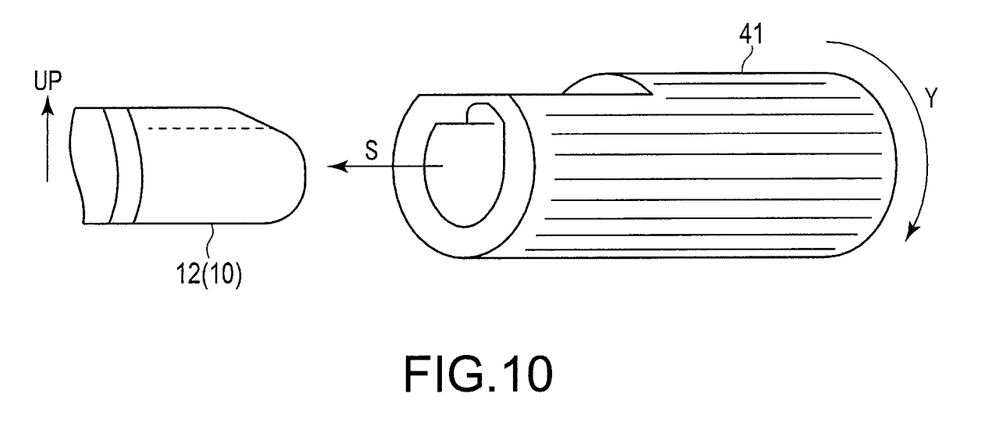
FIG. 10 is a conceptual diagram of the cover removal tool being fitted onto the distal end cover.
Figure 11:
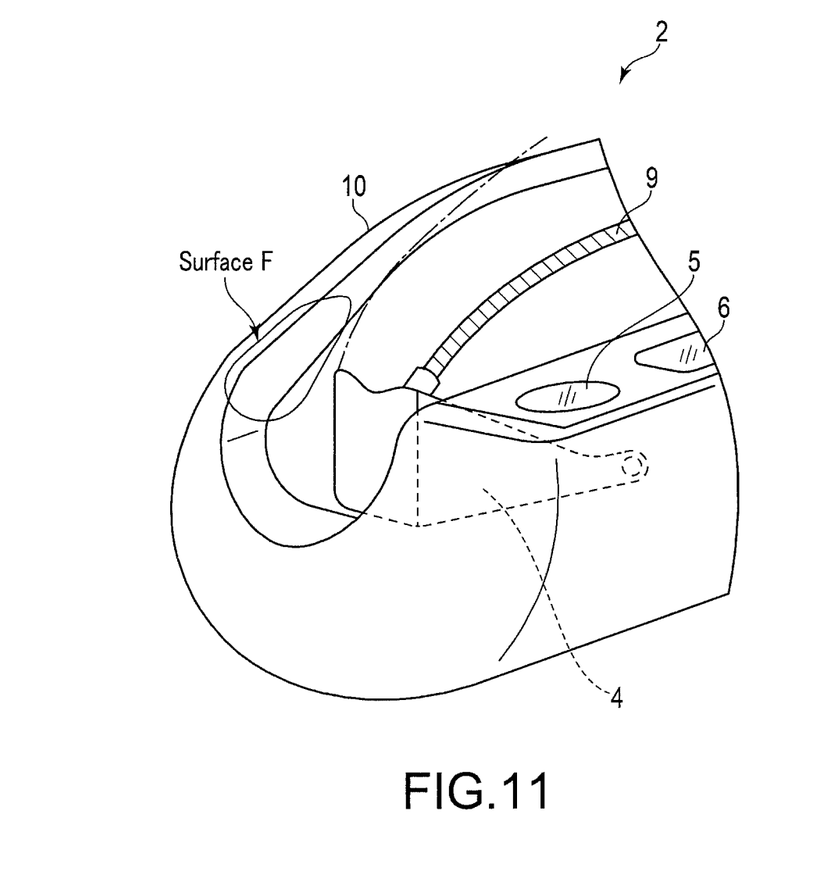
FIG. 11 is a diagram showing the area of the distal end cover that is pressed by the cover removal tool.

Now, the removal of the distal end cover 12 from the distal end assembly 2 will be explained with reference to FIGS. 6A, 6B to 11. FIG. 6A is a diagram showing the structure of a cover removal tool 41, when viewed from the front. FIG. 6B is a cross section showing the structure of the cover removal tool 41 when viewed from its side. FIG. 7 is a cross section of the distal end cover 12 attached to the distal end assembly 2, with the cover removal tool 41 fitted thereon. FIG. 8 is a cross section of the distal end cover 12 with the cover removal tool 41 fitted thereon, before the removal. FIG. 9 is a cross section of the distal end cover 12 with the cover removal tool 41 fitted thereon, when being removed. FIG. 10 is a conceptual diagram of the cover removal tool 41 being fitted onto the distal end cover 12. FIG. 11 is a diagram showing the area of the distal end cover 12 that is pressed by the cover removal tool 41.

As illustrated in FIGS. 6A and 6B, the cover removal tool 41 according to the present application is shaped into a column having a rectangular cross section, formed of a resin stiffer than the resin of the distal end cover 12, or a hard material such as a metallic material. On one end of the cover removal tool 41 is formed a fit hole 41d, which is a portion that is to be fitted to envelop the distal end cover 12. This fit hole 41d includes a surface P that is the bottom surface of the hole with which the tip of the distal end cover 12 is to be brought into contact, and a surface Q that is the inner surface of the fit hole 41d with which the peripheral surface of the distal end cover 12 is to be brought into contact. The cover removal tool 41 illustrated in FIG. 10 is different from the one illustrated in FIG. 6B only in the outer shape. FIG. 10 shows an example of the cover removal tool 41 having a cylindrical outer shape, with multiple slip prevention grooves provided in the peripheral surface. Part of the peripheral surface is left as a flat surface so as to serve as a visible reference position for insertion. As a reference, a word such as "UP" may be used, or an arrow indicating the twist direction may be engraved. As discussed above, the outer shape of the cover removal tool 41 is not limited to any particular form.

In order to remove the distal end cover 12, the fit hole 41d is provided with a protrusion 41a that protrudes so as to break the brittle portion 10h of the first cover 10 and to plastically deform the first cover 10. The protrusion 41a has a width that is insertable between a gap of a distance D between the observation surface 3b and the first cover 10, and a length that is insertable into a swing base space (extending over the opening) without touching the swing base 4.

The fit hole 41d has retraction space 41c, which extends and is curved into the bottom of the protrusion 41a so that the broken portion of the distal end cover 12 can be collected therein. The area 41b of this protrusion 41a is to be in contact with the surface F of the distal end cover 12 in FIG. 11. At the same time, the outer peripheral surface of the distal end cover 12 is fitted to the surface Q without any gap therebetween, as illustrated in FIG. 8.

The cover removal tool 41 is configured so that, when it is fitted, the top slanted surface 41e of the protrusion 41a is positioned above (not in contact with) the moving range of the outermost portion of the rising swing base 4 which is indicated by a dashed-two dotted line, leaving a gap x. With such configuration, the fitted cover removal tool 41 will not come into contact with the swing base 4, no matter which rising position the swing base 4 stays at.

When removing the distal end cover 12 from the distal end assembly 2, the cover removal tool 41 is first fitted, as indicated by arrow S in FIG. 10, to cover the distal end cover 12. Here, the cover removal tool 41 is slid onto the distal end cover 12 until the tip of the distal end cover 12 touches the surface P of the fit hole 41d, as illustrated in FIG. 7.

Then, the cover removal tool 41 that has been fitted on as illustrated in FIG. 8 is twisted in the direction indicated by arrow Y. During this twist, the cover removal tool 41 is pressed in the twist direction with the area 41b of the protrusion 41a in contact with the surface F of the first cover 10. This increases the distance D between the observation surface 3b and the first cover 10 to a distance D1, as illustrated in FIG. 9, and breaks the brittle portion 10h of the first cover 10. As a result, the first cover 10 is plastically deformed and opens outwardly. The surface F is a surface or area of the distal end cover 12 in the vicinity of the edge portion of the opening 10b. When pressing force is applied to this portion in the peripheral direction, the cover portion can be pulled and stretched out. With such plastic deformation, at least one of the locking holes 10a of the first cover 10 is released from the locking pin 3e and comes off of the pin.

As mentioned earlier, the cover removal tool 41 is formed of a hard material. This means that the stress produced on the protrusion 41a of the cover removal tool 41 when twisted around the longitudinal axis of the distal end assembly 2 (flexible tube) can withstand a greater stress than the stress that deforms the distal end cover 12 (first cover 10). Thus, the protrusion 41a would not be damaged.

After this plastic deformation, the cover removal tool 41 is pulled out of the distal end assembly 2. Depending on how the first cover 10 is broken, the cover removal tool 41 may be pulled out together with the broken first cover 10, or the first cover 10 may remain caught in the distal end assembly 2. In the latter case, the first cover 10 can be easily pinched with the fingers and removed from the distal end assembly 2. Thereafter, the elastic second cover 11 can be pulled out of and removed from the distal end assembly 2. The first cover 10, which is broken by the cover removal tool 41 and remaining in the unwashed distal end assembly 2, and the elastic second cover 11 do not have to be pinched directly with the fingers, but may be easily removed with forceps or the like. This ensures hygienic safety for the operator and surgical staff.

The distal end cover 12 according to the present embodiment is described as a structure having separate components of the first cover 10 and the second cover 11, but is not limited to a cover having separate components. That is, as long as at least one of the locking holes 10a in the plastically deformed first cover 10 comes off of the locking pins 3e at the time of removal using the cover removal tool 41, the first cover 10 and the second cover 11 may be uniformly constituted.

As discussed above, according to the present embodiment, simply by fitting and twisting the cover removal tool 41 onto the distal end cover 12 which is attached to the distal end assembly 2, the distal end cover breaks by plastic deformation, thereby allowing for easy removal of the distal end cover 12 from the distal end assembly 2. Thus, without breaking the unwashed distal end cover 12 directly with the fingers, the removal can be readily achieved. Furthermore, the first cover 10 that has been broken and is remaining in the distal end assembly 2, and the second cover 11 formed of an elastic material can be removed with forceps or the like. Thus, the distal end cover 12 can be removed without direct contact with the hands. Furthermore, because the removed distal end cover 12 has been partially broken and plastically deformed, the reuse of the cover even after washing can be prevented, and therefore the patient safety can be ensured.

In addition, with the rotation preventing convex portions 10f engaged with the rotation regulation sections 3c and 3d, the distal end cover 12 can be prevented from rotating, and the locking pins 3e and the locking holes 10a serve as prevention of detachment of the distal end cover 12 from the distal end assembly 2. The second cover 11, which has tightening elastic force, presses the fit groove 11b and the locking holes 10a, and makes them difficult to be detached from the distal end assembly 2. The distal end cover 12, which includes the first cover 10 and second cover 11 both having insulation properties, can be fitted onto the distal end assembly 2 entirely from the tip of the base member 3 to the insulation ring 13, except for the opening 10b. Thus, the high-frequency current can be prevented from leaking not only from the portion covered by the distal end cover 12, but also from the proximal side of the second cover 11, or in other words, from the proximal side of the distal end cover 12.

First Modification Example of First Embodiment

Figure 13:
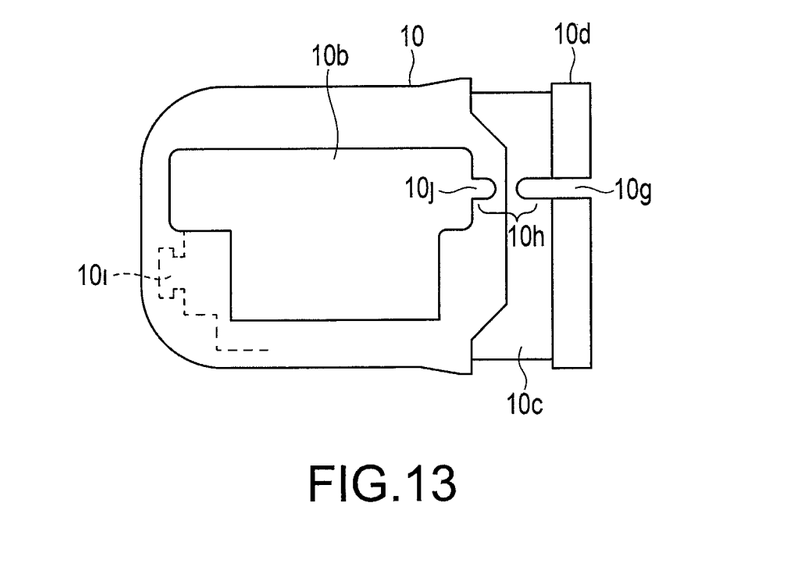
FIG. 13 is a diagram showing the outer appearance of the distal end cover according to the first modification example of the first embodiment, when viewed from above.
Figure 14:
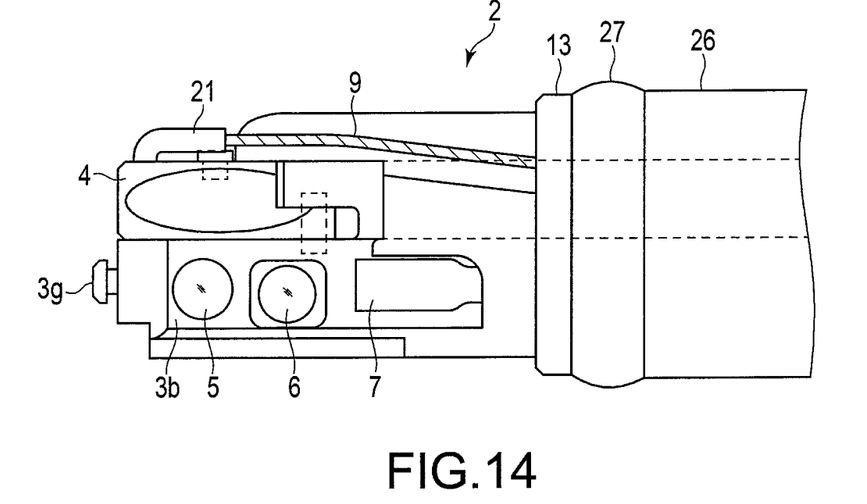
FIG. 14 is a diagram showing the outer appearance of the distal end assembly provided with a locking portion according to the first modification example, when viewed from above.
Figure 15:
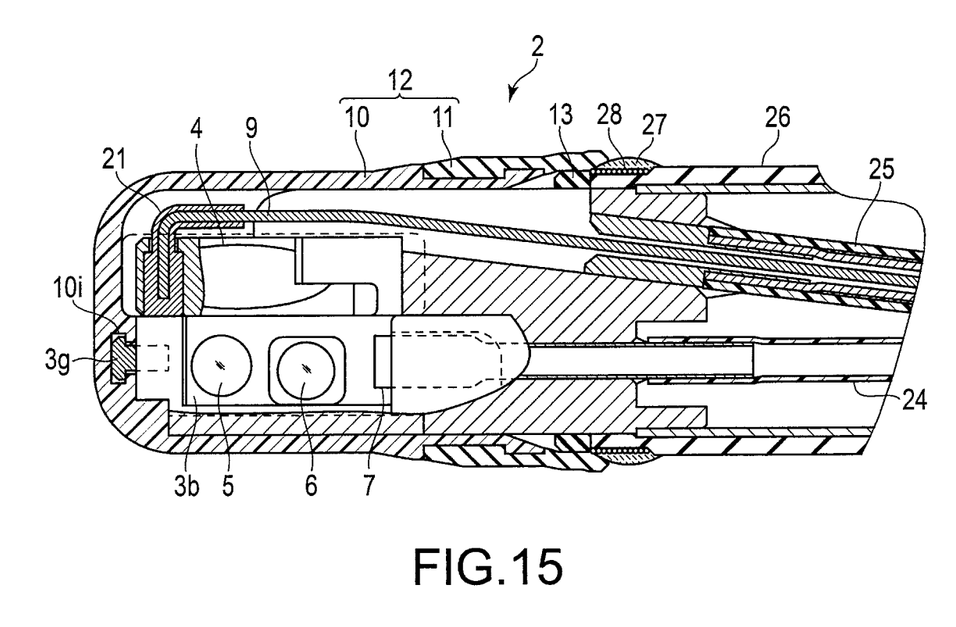
FIG. 15 is a cross section of the structure of the distal end assembly with the distal end cover attached, when viewed from above.

FIG. 13 is a diagram showing the outer appearance of a distal end cover according to the first modification example of the first embodiment, when viewed from above. FIG. 14 is a diagram showing the outer appearance of a distal end assembly provided with an locking portion according to the first modification example, when viewed from above. FIG. 15 is a cross section of the structure of the distal end assembly with the distal end cover attached, when viewed from above. This modification example is different from the above first embodiment only in the first locking portion (locking pin 3e) of the first embodiment. Except for the second locking portion in the first modification example, the same or similar components will be indicated by the same symbols, and detailed descriptions thereof will be omitted.

According to this modification example, a T-locking pin 3g [second locking portion] is provided on the distal side of the distal end assembly 2 to be engaged with the first cover 10, and a T-groove 10i is provided in the first cover 10 to fit on the T-locking pin 3g.

As illustrated in FIG. 14, the T-locking pin 3g is arranged on the distal surface of the distal end assembly 2 which is in contact with the observation surface 3b. The head portion (in the shape of a disk, for example) of the T-locking pin 3g is subjected to a chamfering process for its periphery so as to be tapered to a narrow tip. This makes the T-locking pin 3g easy to fit in the T-groove 10i of the first cover 10 that is illustrated in FIG. 13.

The removal of the distal end cover 12 in this modification example is basically the same as the first embodiment. The cover removal tool 41 is fitted onto the distal end cover 12 by sliding the cover removal tool 41 in until the tip of the distal end cover 12 comes into contact with the surface P of the fit hole 41d. Thereafter, by twisting the cover removal tool 41 and pushing it in the twist direction with the area 41b of the protrusion 41a in contact with the surface F of the first cover 10, the distance between the observation surface 3b and the first cover 10 increases as illustrated in FIG. 9, causing plastic deformation. In accordance with this increase in the distance by the plastic deformation, the tip portion of the first cover 10 is also twisted and the T-groove 10i is stretched out, as a result of which the locking pin 3g comes off.

Then, the cover removal tool 41 is pulled out of the distal end assembly 2. Depending on how the first cover 10 is broken, the cover removal tool 41 may be pulled out together with the broken first cover 10, or the first cover 10 may remain caught in the distal end assembly 2. In the latter case, the first cover 10 can be easily pinched with the fingers and removed from the distal end assembly 2. Thereafter, the elastic second cover 11 is pulled and removed from the distal end assembly 2. In this modification example, the broken first cover 10 and the elastic second cover 11 can be easily removed using the forceps or the like.

This modification example can produce similar effects to the above-discussed first embodiment. In the modification example, the T-locking pin 3g that serves as the second locking portion is provided on the tip surface of the distal end assembly 2. In other words, the pin is arranged in the longitudinal direction of the distal end assembly 2, which reduces the diameter of the distal end assembly 2 in comparison with the structure in which a pin is arranged on the side surface. This arrangement therefore contributes to the reduction of the diameter of the flexible tube.

In the distal end cover 12 of this modification example, the second cover 11 and the insulation ring 13 are tightly attached to each other. Thus, the high-frequency current will not be leaked outside, but will be propagated and returned within the flexible tube of the endoscope. For this reason, the high-frequency current will not be leaked from the back portion of the distal end cover 12 which cannot be viewed by the operator. Even if the distal end cover 12 touches the living tissue other than the treatment target area in the lumen, the possibility of inflicting a burn or any other damage can be significantly reduced.

Second Modification Example of First Embodiment

Figure 16A:
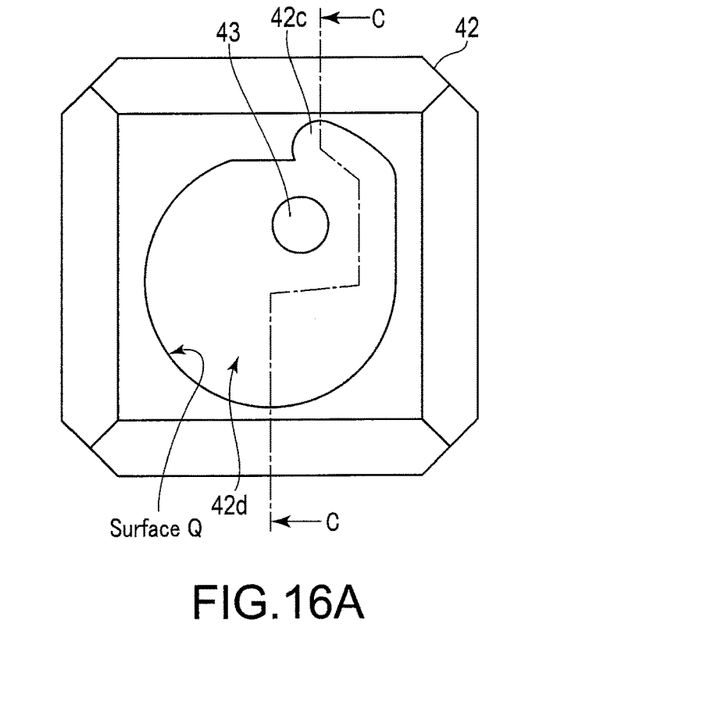
FIG. 16A is a diagram showing the structure of the cover removal tool according to the second modification example of the first embodiment, when viewed from the front.
Figure 16B:
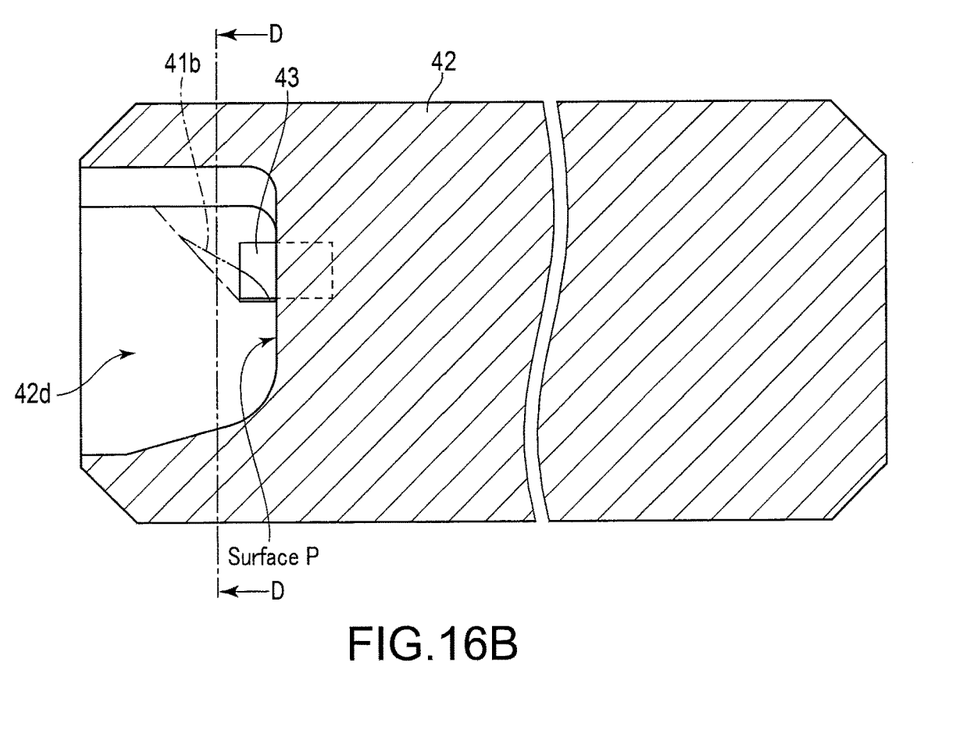
FIG. 16B is a cross section showing the structure of the cover removal tool when viewed from its side.

FIG. 16A is a diagram showing the structure of a cover removal tool 42 according to the second modification example of the first embodiment, when viewed from the front. FIG. 16B is a cross section showing the structure of the cover removal tool 42 when viewed from its side. This modification example is different from the above first embodiment only in the protrusion 41a of the first embodiment. Other components, if they are similar to those of the first embodiment, will be indicated by the same symbols, and detailed descriptions thereof will be omitted.

The cover removal tool 42 according to this modification example is provided with, in place of the protrusion 41a, a columnar separator pin 43 in such a manner as to extend in the longitudinal direction from the surface P in the fit hole 41d. This separator pin 43 is set up at a position corresponding to the area 41b of the aforementioned protrusion 41a, where the separator pin 43 comes into contact with the aforementioned surface F of the first cover 10.

When the distal end cover 12 is removed from the distal end assembly 2 in this modification example, first, the cover removal tool 42 is slid in the direction indicated by the arrow S in FIG. 10 to fit on the distal end cover 12. Here, the cover removal tool 42 is moved in until the tip of the distal end cover 12 touches the surface P in FIG. 16B.

Next, in the state of being fitted, the cover removal tool 42 is twisted in the same direction as arrow Y indicated in FIG. 8. During this twist, the separator pin 43 pushes the surface F of the first cover 10 in the twist direction to widen the distance between the observation surface 3b and the first cover 10 as illustrated in FIG. 9. As a result, the brittle portion 10h of the first cover 10 is broken, and the first cover 10 is plastically deformed to open outwardly.

After the plastic deformation is achieved, the cover removal tool 42 is pulled out of the distal end assembly 2. Depending on how the first cover 10 is broken, the cover removal tool 42 may be pulled out together with the broken first cover 10, or the first cover 10 may remain caught in the distal end assembly 2. In the latter case, the first cover 10 can be easily pinched with the fingers and removed from the distal end assembly 2. Thereafter, the elastic second cover 11 is pulled and removed from the distal end assembly 2.

This modification example can attain similar effects to the above-discussed first embodiment. Furthermore, the structure is simpler in comparison to the aforementioned protrusion 41a according to the first embodiment, with the separator pin 43 provided on the bottom hole surface of the cover removal tool 42. As a result, the design and production can be simplified. Even when changes are to be made to the design of the first cover 10, such changes can be flexibly dealt with simply by changing the arrangement position of the separator pin 43.

The present invention offers a distal end cover for an endoscope, which is easily attachable to the distal end assembly of the insertion section of the endoscope, has a function of preventing the leakage of the high-frequency current, and is removable with a simple operation.

The invention claimed is:

1. An endoscopic cover removal tool configured to remove a distal end cover having an opening, the distal end cover being attached to a distal end assembly arranged at a distal end of an insertion section of an endoscope configured to to be inserted into a lumen, the cover removal tool comprising:
    an enclosure including a fit hole, the enclosure being configured to cover a distal-most periphery of the distal end cover when the distal end cover is fitted in the fit hole; and
    a protrusion extending from an inner surface of the enclosure, the protrusion being configured to enter the opening of the distal end cover when the enclosure is twisted around a longitudinal axis of the distal end cover when the distal end cover is fitted in the enclosure to press an edge of the opening in a peripheral direction.

2. The endoscopic cover removal tool according to claim 1, wherein the distal end cover further having one or more slits defining a weakened portion; and
    the protrusion is configured to come in contact with part of the edge of the opening of the distal end cover, and to press the part of the edge in the peripheral direction to break the weakened portion.

3. The endoscopic cover removal tool according to claim 1, wherein
    the endoscope includes a swing base that swings a distal end of a treatment tool that is inserted into the insertion section, and
    the protrusion is positioned so as to be inserted into a swing base space provided in the distal end cover.

4. The endoscopic cover removal tool according to claim 3, wherein the protrusion is provided in such a manner as to avoid a region in which the swing base is positioned when the distal end cover attached to the distal end assembly comes into contact.

5. The endoscopic cover removal tool according to claim 4, wherein the protrusion is provided in such a manner as to avoid a region in which the swing base is positioned in a raised state when the distal end cover attached to the distal end assembly comes into contact.

6. The endoscopic cover removal tool according to claim 1, wherein the protrusion is configured to withstand a stress greater than a stress that is produced in the protrusion when the enclosure is twisted around the longitudinal axis of the distal end cover.

7. The endoscopic cover removal tool according to claim 1, wherein
    the distal end cover is attached to the distal end assembly via a lock portion, and
    when the enclosure is twisted around the longitudinal axis of the distal end cover, the protrusion withstands a stress greater than a stress that can release lock of the lock portion between the distal end cover and the distal end assembly.

8. The endoscopic cover removal tool according to claim 1, wherein the protrusion has a length such that the protrusion is insertable in the opening when the distal end cover is fitted in the enclosure.

9. An endoscopic system comprising:
    an endoscope including an insertion section configured to to be inserted into a lumen, and a distal end cover having an opening, the distal end cover being attached to a distal end assembly arranged at a distal end of the insertion section; and
    a distal cover removal tool, comprising:
        an enclosure including a fit hole, the enclosure being configured to cover a distal-most periphery of the distal end cover when the distal end cover is fitted in the fit hole; and
        a protrusion extending from an inner surface of the enclosure, the protrusion being configured to enter the opening of the distal end cover when the enclosure is twisted around a longitudinal axis of the distal end cover when the distal end cover is fitted in the enclosure to press an edge of the opening in a peripheral direction.

10. The endoscopic system according to claim 9, wherein the protrusion has a length such that the protrusion is insertable in the opening when the distal end cover is fitted in the enclosure.

* * * * *